US00PP18297P2

(12) United States Plant Patent
Meszaros

(10) Patent No.: US PP18,297 P2
(45) Date of Patent: Dec. 11, 2007

(54) ***LANTANA* PLANT NAMED 'LIBERTY BELL'**

(50) Latin Name: *Lantana camara*
Varietal Denomination: Liberty Bell

(75) Inventor: Debra Meszaros, Riverhead, NY (US)

(73) Assignee: Advanced Plant Technologies LLC, Riverhead, NY (US)

( * ) Notice: Subject to any disclaimer, the term of this patent is extended or adjusted under 35 U.S.C. 154(b) by 0 days.

(21) Appl. No.: 11/438,532

(22) Filed: May 22, 2006

(51) Int. Cl.
*A01H 5/00* (2006.01)

(52) U.S. Cl. ..... Plt./227
(58) Field of Classification Search ..... None
See application file for complete search history.

*Primary Examiner*—Wendy C Haas
(74) *Attorney, Agent, or Firm*—C. A. Whealy

(57) ABSTRACT

A new and distinct cultivar of *Lantana* plant named 'Liberty Bell', characterized by its compact, mounding and outwardly spreading growth habit; freely branching plant habit; yellow-green and dark green variegated foliage; freely flowering habit; and yellow and white-colored flowers.

2 Drawing Sheets

Botanical designation: *Lantana camara.*
Cultivar denomination: 'Liberty Ball'.

BACKGROUND OF THE INVENTION

The present invention relates to a new and distinct cultivar of *Lantana,* botanically known as *Lantana camara,* and hereinafter referred to by the name 'Liberty Bell'.

The new *Lantana* is a product of a planned breeding program conducted by the Inventor in Riverhead, N.Y. The objective of the breeding program is to create new freely-branching and freely-flowering *Lantana* cultivars with attractive foliage and flower coloration.

The new *Lantana* is a naturally-occurring whole plant mutation of the *Lantana camara* cultivar Silvermound, not patented. The new *Lantana* was discovered and selected by the Inventor from within a population of plants of 'Silvermound' in a controlled environment in Riverhead, N.Y. on May 4, 2004.

Asexual reproduction of the new *Lantana* by terminal cuttings in a controlled environment in Riverhead, N.Y. since November, 2004, has shown that the unique features of this new *Lantana* are stable and reproduced true to type in successive generations.

SUMMARY OF THE INVENTION

The cultivar Liberty Bell has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Liberty Bell'. These characteristics in combination distinguish 'Liberty Bell' as a new and distinct cultivar of *Lantana:*

1. Compact, mounding and outwardly spreading growth habit.
2. Freely branching plant habit.
3. Yellow-green and dark green variegated foliage.
4. Freely flowering habit.
5. Yellow and white-colored flowers.

Plants of the new *Lantana* can be compared to plants of the parent, the cultivar Silvermound. Plants of the new *Lantana* differ from plants of the cultivar Silvermound in the following characteristics:

1. Plants of the new *Lantana* are more compact and less vigorous than plants of the cultivar Silvermound.
2. Plants of the new *Lantana* are more freely branching and have shorter internodes then plants of the cultivar Silvermound.
3. Plants of the new *Lantana* have smaller leaves than plants of the cultivar Silvermound.
4. Plants of the new *Lantana* have variegated foliage whereas plants of the cultivar Silvermound have solid green-colored foliage.

Plants of the new *Lantana* can be compared to plants of the *Lantana camara* cultivar Samantha, not patented. In side-by-side comparison conducted in Riverhead, N.Y., plants of the new *Lantana* differed from plants of the cultivar Samantha in the following characteristics:

1. Plants of the new *Lantana* were more compact and less vigorous than plants of the cultivar Samantha.
2. Plants of the new *Lantana* were more freely branching and had shorter internodes than plants of the cultivar Samantha.
3. Plants of the new *Lantana* had smaller leaves than plants of the cultivar Samantha.
4. Plants of new *Lantana* and the cultivar Samantha differed in flower color as plants of the cultivar Samantha had golden yellow-colored flowers.

BRIEF DESCRIPTION OF THE PHOTOGRAPHS

The accompanying colored photographs illustrate the overall appearance of the new *Lantana,* showing the colors as true as it is reasonably possible to obtain in colored reproductions of this type. Colors in the photographs may differ slightly from the color values cited in the detailed botanical description which accurately describe the colors of the new *Lantana.*

The photograph on the first sheet comprises a side perspective view of a typical flowering plant of 'Liberty Bell' grown in a container.

The photograph on the second sheet is a close-up view of typical inflorescences and leaves of 'Liberty Bell'.

DETAILED BOTANICAL DESCRIPTION

The photographs and following observations, measurements and values describe plants grown in Riverhead, N.Y. in a polyethylene-covered greenhouse during the spring and summer under conditions which closely approximate commercial production. During the production of the plants, day temperatures were about 24° C., night temperatures were about 20° C. and light levels ranged from 3,000 to 8,000 foot-candle. Plants were about three months old when the photographs and the description were taken. In the detailed description, color references are made to The Royal Horticultural Society Colour Chart, 1995 Edition, except where general terms of ordinary dictionary significance are used.

Botanical classification: *Lantana camara* cultivar Liberty Bell.

Parentage: Naturally-occurring whole plant mutation of the *Lantana camara* cultivar Silvermound, not patented.

Propagation:

*Type.*—By terminal cuttings.

*Time to initiate roots, summer.*—About 10 days at temperatures of 24° C.

*Time to initiate roots, winter.*—About 14 days at temperatures of 22° C.

*Time to produce a rooted young plant, summer.*—About 28 days at temperatures of 24° C.

*Time to produce a rooted young plant, winter.*—About 32 days at temperatures of 22° C.

*Root description.*—Fibrous; white in color.

*Rooting habit.*—Freely branching; dense.

Plant description:

*Plant habit.*—Compact; initially upright, the outwardly spreading and mounding. Freely branching; about ten to twelve lateral branches per plant; pinching enhances lateral branch development; dense and bushy growth habit.

*Plant height.*—About 13 cm.

*Plant diameter.*—About 30 cm to 35 cm.

Lateral branch description:

*Length.*—About 16 cm.

*Diameter.*—About 2 mm.

*Internode length.*—About 1 cm.

*Strength.*—Flexible but strong.

*Texture.*—Smooth, glabrous.

*Color, immature.*—144B.

*Color, mature.*—close to 165A.

Foliage description:

*Arrangement.*—Opposite, simple.

*Length.*—About 2.8 cm.

*Width.*—About 1.1 cm.

*Shape.*—Roughly ovate.

*Apex.*—Acute.

*Base.*—Obtuse.

*Margin.*—Serrate.

*Texture, upper and lower surfaces.*—Coarse, rough; pubescent.

*Venation pattern.*—Pinnate.

*Color.*—Developing and fully developed foliage, upper surface: Towards the margins, 145C; random central sectors, 147A; venation, 157A to 144C. Developing and fully developed foliage, lower surface: Towards the margins, 145C; random central sectors, 146A; venation, 157A to 145B.

*Petiole.*—Length: About 3 mm. Diameter: About 1 mm. Texture, upper and lower surfaces: Smooth, glabrous. Color, upper and lower surfaces: 145B or 150D.

Flower description:

*Flower arrangement and habit.*—Solitary salverform flowers arranged in axially umbels; flowers face mostly upward or outward. Freely flowering habit with potentially two inflorescences developing per node.

*Natural flowering season.*—Spring until frost in the autumn; flowering continuous during this period.

*Flower longevity on the plant.*—About two to three weeks. Flowers not persistent.

*Fragrance.*—Mildly sweet.

*Flowers.*—Appearance: Flared trumpet, corolla fused, four-parted Diameter: About 3 cm. Depth (height): About 2 cm.

*Flower buds.*—Length: About 3 mm. Diameter: About 0.4 mm. Shape: Elongate, oblong. Color: 144C.

*Color.*—Arrangement: Single whorl of four fused petals. Petal length: About 1 cm. Petal width: About 1 cm. Petal shape: Roughly ovoid. Petal apex: Rounded. Petal margin: Entire. Petal texture, upper and lower surfaces: Smooth, velvety. Color: Petal, when opening, upper and lower surfaces: 11D. Petal, fully opened, upper and lower surfaces: 155C. Throat: 11D. Tube: 155C.

*Calyx.*—Arrangement: One single calyx tube per flower. Calyx length: About 3 mm. Calyx width: About 2 mm. Apex: Rounded. Texture: Pubescent. Color, upper and lower surfaces: Close to 144C.

*Peduncles.*—Length: About 2 cm to 3 cm. Diameter: About 1 mm to 2 mm. Strength: Flexible, but strong. Texture: Pubescent. Color: 144B.

*Pedicels.*—Length: Less than 1 mm. Diameter: Less than 1 mm. Color: Close to 144B.

*Reproductive organs.*—Stamens: Quantity/arrangement: Four per flower, adnate to floral tube. Anther shape: Ovoid. Anther length: About 0.5 mm. Anther color: 9A. Pollen amount: Moderate. Pollen color: 9A. Pistils: Quantity: One per flower. Stigma shape: Bi-lobed. Style length: About 2 mm. Style color: 150D. Ovary color: 149D. Seeds: Size: About 4 mm by 4 mm. Color, immature: 144D. Color, mature: 202A.

Temperature tolerance: Plants of the new *Lantana* have been observed to tolerate temperatures from about 8° C. to about 35° C.

Pathogen/pest resistance: Plants of the new *Lantana* have not been observed to be resistant to pests and pathogens common to *Lantanas*.

It is claimed:

1. A new and distinct *Lantana* plant named 'Liberty Bell' as illustrated and described.

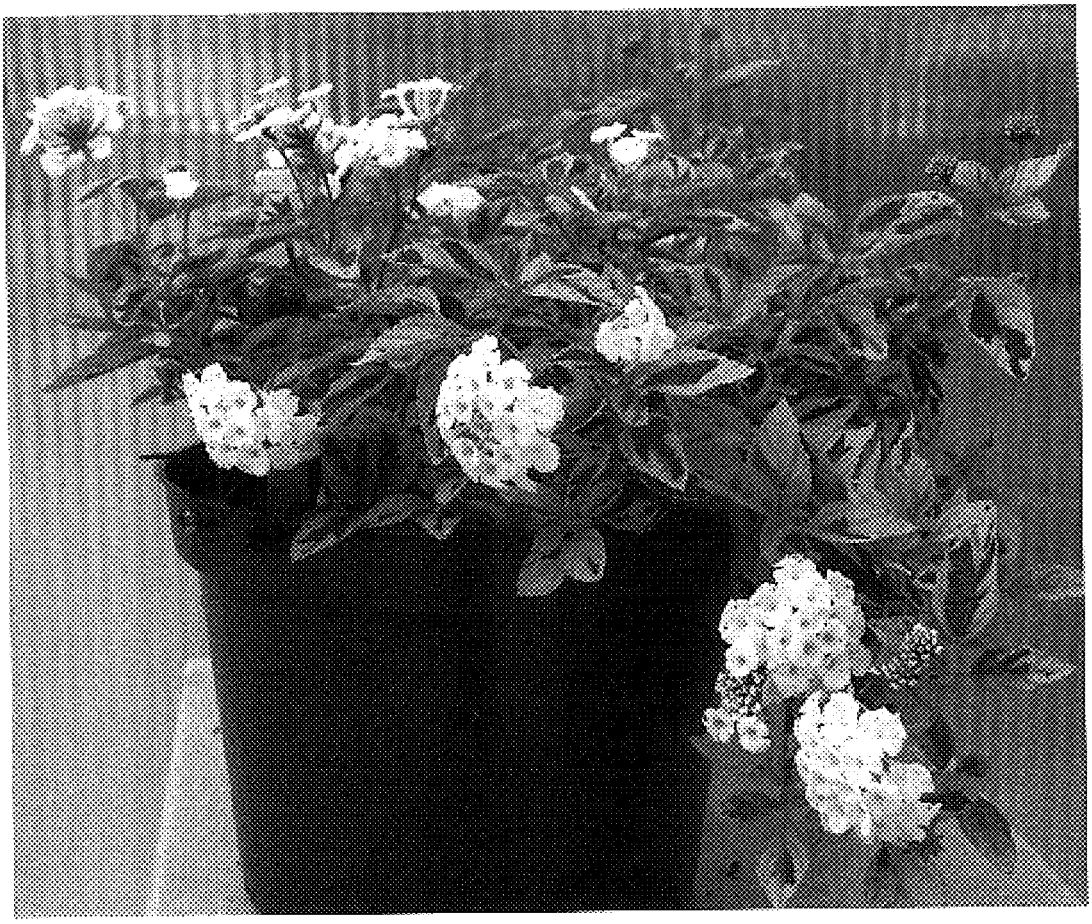

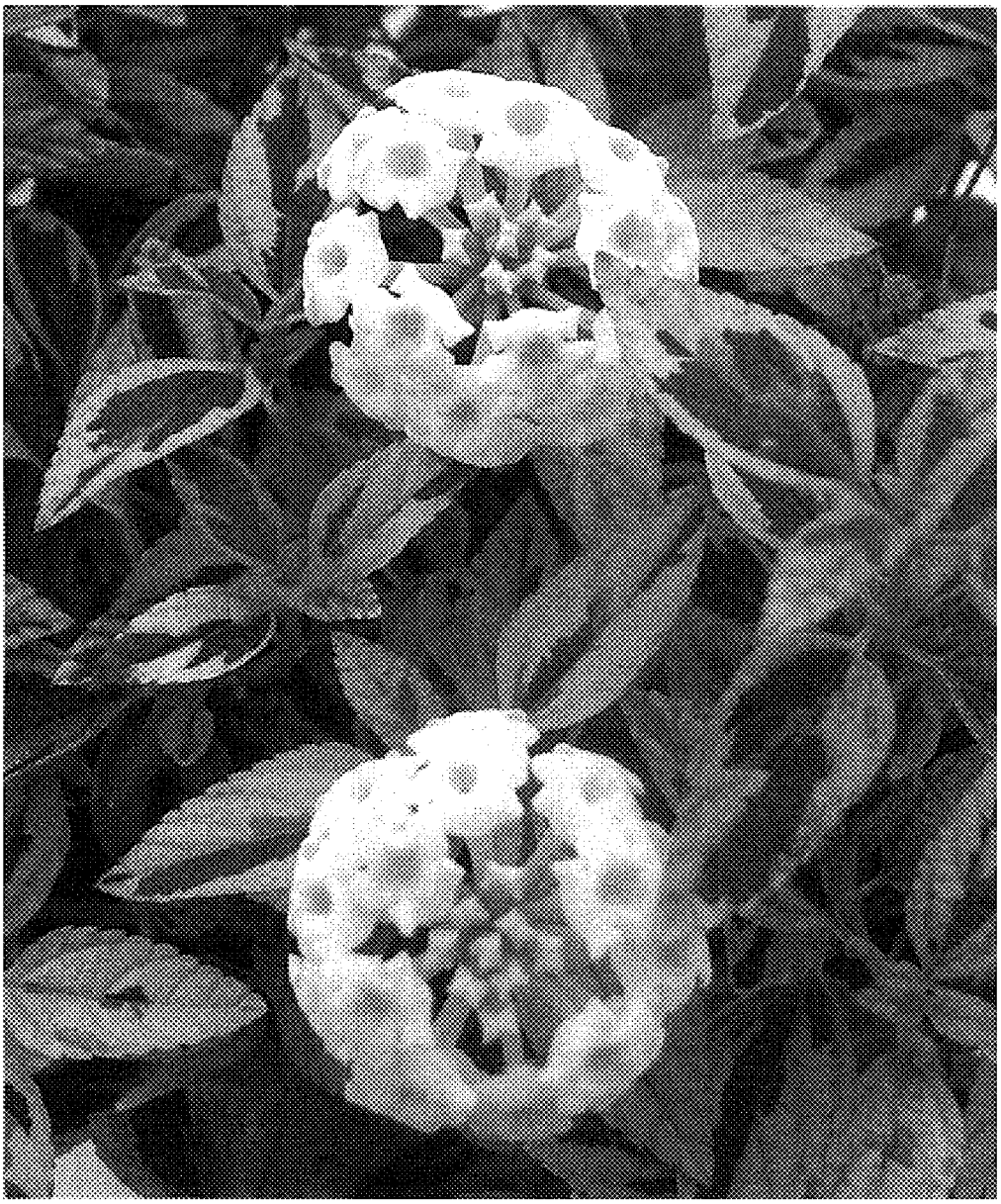

* * * * *